United States Patent
Kauffman et al.

(10) Patent No.: US 7,043,967 B2
(45) Date of Patent: May 16, 2006

(54) SENSOR DEVICE FOR MONITORING THE CONDITION OF A FLUID AND A METHOD OF USING THE SAME

(75) Inventors: Robert E. Kauffman, Centerville, OH (US); James D. Wolf, Kettering, OH (US)

(73) Assignee: University of Dayton, Dayton, OH (US)

( * ) Notice: Subject to any disclaimer, the term of this patent is extended or adjusted under 35 U.S.C. 154(b) by 0 days.

(21) Appl. No.: 10/260,754

(22) Filed: Sep. 30, 2002

(65) Prior Publication Data

US 2004/0060344 A1    Apr. 1, 2004

(51) Int. Cl.
    *G01N 11/00*    (2006.01)
(52) U.S. Cl. .................. 73/53.01; 73/53.04; 73/295
(58) Field of Classification Search ............... 73/53.1, 73/295, 292, 53.01, 53.04
    See application file for complete search history.

(56) References Cited

U.S. PATENT DOCUMENTS

| | | | | |
|---|---|---|---|---|
| 3,580,263 | A | * | 5/1971 | Hughes ................. 73/309 |
| 3,710,237 | A | * | 1/1973 | Watson et al. ........... 324/446 |
| 4,601,201 | A | * | 7/1986 | Oota et al. .............. 73/304 C |
| 4,646,070 | A | * | 2/1987 | Yasuhara et al. ......... 340/603 |
| 4,692,698 | A | * | 9/1987 | Lewis ................... 324/204 |
| 4,720,997 | A | * | 1/1988 | Doak et al. ............. 73/295 |
| 4,744,879 | A | | 5/1988 | Kaminaga et al. |
| 4,764,258 | A | | 8/1988 | Kauffman |
| 5,071,527 | A | | 12/1991 | Kauffman |
| 5,262,732 | A | * | 11/1993 | Dickert et al. ............ 324/672 |
| 5,765,994 | A | | 6/1998 | Barbier |
| 5,933,016 | A | | 8/1999 | Kauffman et al. |
| 6,095,371 | A | | 8/2000 | Mooney |
| 6,202,486 | B1 | * | 3/2001 | Kemp .................. 73/295 |
| 6,278,282 | B1 | | 8/2001 | Marszalek |
| 6,324,899 | B1 | | 12/2001 | Discenzo |
| 6,421,588 | B1 | | 7/2002 | Janata |
| 2001/0035827 | A1 | * | 11/2001 | Snelling ............... 340/622 |

FOREIGN PATENT DOCUMENTS

| | | |
|---|---|---|
| EP | 0675 369 A | 10/1995 |
| EP | 1 098 197 A | 5/2001 |
| GB | 1 418 918 A | 12/1975 |

* cited by examiner

*Primary Examiner*—Hezron Williams
*Assistant Examiner*—Jacques M. Saint-Surin
(74) *Attorney, Agent, or Firm*—Dinsmore & Shohl LLP

(57) ABSTRACT

The present invention is a compact apparatus and method that provides an efficient manner for monitoring the condition and level of a functional fluid directly in operating equipment. A sensor device is provided that includes a plurality of liquid sensors and a plurality of vapor sensors that when used in conjunction with one another at different temperatures, can provide a thorough evaluation of the oxidative degradation, liquid contamination and solid contamination of the fluid to detect the end of the useful life of the fluid. By providing liquid sensors and vapor sensors on the same device, the present invention allows for a compact, efficient, and economically feasible manner to monitor the condition of fluid as well as detecting abnormal operating conditions prior to further component damage and eventual equipment failure.

34 Claims, 7 Drawing Sheets

SENSOR DEVICE FOR MONITORING THE CONDITION OF A FLUID AND A METHOD OF USING THE SAME

STATEMENT REGARDING FEDERALLY SPONSORED RESEARCH OR DEVELOPMENT

This invention was made with government support under Contract No. F33615-98-C-2864 awarded by US Army TACOM Warren, Mich. The Government has certain rights in this invention.

BACKGROUND

The present invention relates generally to fluids and more particularly to an apparatus and method for evaluating the condition of an organic fluid required by operating equipment to perform properly. The condition of a fluid is evaluated based on the degree of basestock oxidative degradation, degree of additive(s) depletion, levels of liquid and solid contaminants, and other parameters that affect the fluid's ability to perform its required functions in operating equipment.

Fluid, such as oil or fuel, is often used to lubricate and cool components of operating equipment as well as remove generated particles from moving surfaces. The fluid circulating in normally operating equipment experiences thermal and oxidative stresses along with a wide range of contamination that slowly decrease the condition of the fluid, i.e., shorten the fluid's useful life. To ensure a fluid with a poor condition does not damage the equipment, fluid change-outs are performed on a regular schedule based on operating time, mileage, or other operational parameters. Since not all equipment of the same type decrease the condition of operating fluid at the same rate, the scheduled change-outs are conservative to ensure no circulating fluid, regardless of the particular equipment operating conditions, is used past the end of its useful life. On occasion, worn or damaged components as well as external forces or contaminants cause equipment to operate abnormally resulting in accelerated oxidation and/or contamination of the circulating fluid. If the resulting deterioration of the fluid's condition is not detected, then further component damage or possible equipment failure will result after the useful life of the fluid has expired. Therefore, a complete analysis of the fluid should be conducted periodically to monitor fluid condition in order to ensure the fluid is changed out prior to the end of its useful life and to detect abnormally operating equipment to prevent further component damage or equipment failure.

However, for most operating equipment frequent fluid sampling is impractical due to the remote location of the equipment, equipment design, lack of maintenance personnel and/or cost of operating an oil analysis program. In addition, some abnormal operating conditions such as internal component fires or seal rupture require immediate detection to prevent equipment failure and can not be monitored successfully with periodic sampling no matter how frequent.

Accordingly, there is a need in the art for an efficient way to continuously monitor the condition of the fluid to determine the proper fluid change out schedule for both normally and abnormally operating equipment and to detect abnormal conditions prior to further component damage or equipment failure.

SUMMARY OF THE INVENTION

This need is met by the present invention wherein a method and an apparatus are provided that monitor the condition of the fluid by measuring a number of parameters of the fluid. The present invention uses multiple sensors to measure the vapor and liquid properties of the fluid at different temperatures and after different fluid treatments. From these measurements, the condition of the fluid can be determined.

In accordance with one embodiment of the present invention, there is provided a sensor device for monitoring the condition of a fluid comprising a member, a plurality of liquid sensors measuring liquid parameters of a fluid coupled to the member, and a plurality of vapor sensors for measuring vapor parameters of a fluid coupled to the member, wherein the plurality of liquid sensors and plurality of vapor sensors are positioned a distance from one another so that the plurality of vapor sensors do not contact the liquid.

In accordance with one embodiment of the present invention, there is provided a sensor device for monitoring the condition of a fluid comprising a member, a plurality of liquid sensors measuring liquid parameters of a fluid coupled to the member, a plurality of vapor sensors for measuring vapor parameters of a fluid coupled to the member, wherein the plurality of liquid sensors and plurality of vapor sensors are positioned a distance from one another so that the plurality of vapor sensors do not contact the liquid, and a display system coupled to the end of the member opposite to the liquid sensors.

In accordance with yet another embodiment of the present invention, there is provided a method for monitoring the condition of a fluid including the steps of providing a sensor device having a plurality of liquid sensors and a plurality of vapor sensors on a member; placing the member in a fluid such that the plurality of liquid sensors are immersed in the fluid and the plurality of vapor sensors do not come in contact with the fluid; measuring at least one parameter of the fluid; analyzing measurements of the fluid at different temperatures; and determining the condition of the fluid.

BRIEF DESCRIPTION OF THE SEVERAL VIEWS OF THE DRAWINGS

The following detailed description of the preferred embodiments of the present invention can be best understood when read in conjunction with the following drawings, where like structure is indicated with like reference numerals and in which.

DETAILED DESCRIPTION

Figure 1:
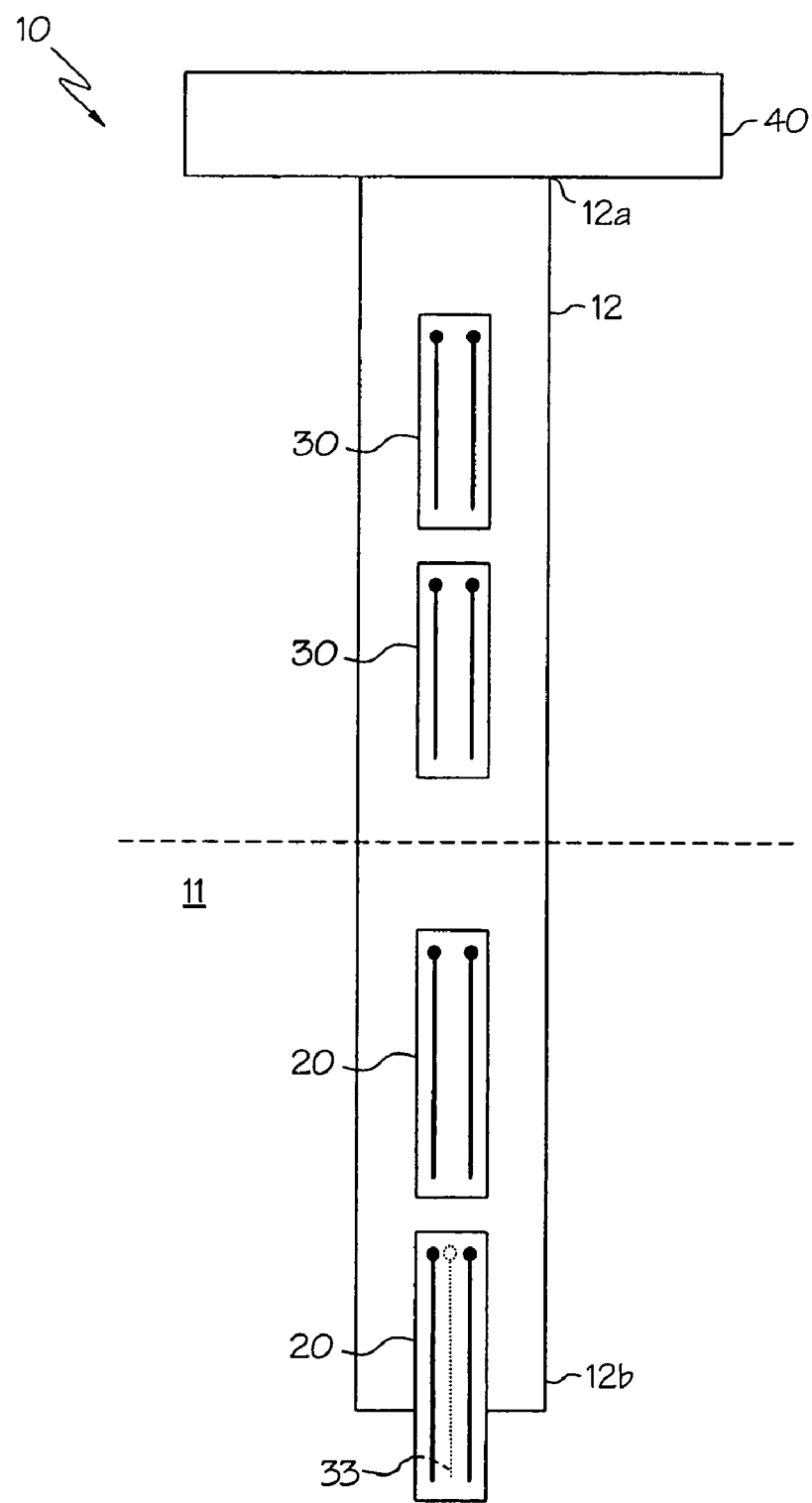
FIG. 1 is a schematic illustration of a sensor device having a plurality of vapor sensors and a plurality of liquid sensors according to one embodiment of the present invention.

Referring to FIG. 1, the present invention is a sensor device 10 that includes a plurality of liquid sensors 20 and a plurality of vapor sensors 30 that when used in conjunction with one another, can provide a thorough evaluation of the fluid to monitor the condition of the fluid. By providing liquid sensors 20 and vapor sensors 30 on the same sensor device 10, the present invention allows for a compact, efficient, and economically feasible manner to monitor the condition of a fluid directly inside the operating equipment, via an on-line/on-board sensor device. The sensor device is adapted to measure fluid level, viscosity, temperature, electrical conductivity, electrochemical activity, water contamination, wear metals, soot buildup, coolant contamination, fluid level, and combinations thereof. Furthermore, the sensor device 10 allows for the lengthening of fluid sampling intervals of the monitored piece of equipment. In addition, the sensor device 10 allows for lengthening the fluid change out intervals of different equipment with the insurance that the useful life of the fluid will not be exceeded due to overuse. Further, the sensor device 10 increases the capabilities of an equipment operator to detect abnormally operating equipment at an earlier stage.

The sensors 20 and 30 are coupled to a member 12 having a first member end 12a and a second member end 12b. In one embodiment, member 12 is made of a conductive material to match the composition of surrounding components such as cast iron, stainless steel, aluminum or any other suitable metal. The member 12 may also be made of a nonconductive material such as tetrafluoroethylene, high density polyethylene, polyimide polymer used for circuit boards, any other plastic or composite material dimensionally and chemically stable at the operating temperature of the monitored equipment, and combinations thereof. Member 12 is sized to be accommodated in the conventional dipstick port used in engines or other operating equipment with a fluid reservoir for checking the level of the operating fluid, such as, for example, oil. Member 12 can be a conventional dipstick.

The number and type of sensors utilized by the sensor device 10 can be pre-selected based on the degradation/contamination mechanisms of the equipment to be monitored. The sensors 20 and 30 are arranged on the member 12 in a manner such that the plurality of liquid sensors 20 may be fully immersed in a fluid 11 while the plurality of vapor sensors 30 do not come into contact with the fluid. Therefore, the vapor sensors 30 only measure parameters of the vapor portion of the fluid. The liquid sensors 20 measure the temperature and electrical properties of the fluid. In one embodiment, the electrical properties are measured using single electrode conductivity and triangular waveform voltammetry methods that are disclosed by U.S. Pat. Nos. 5,933,016 and 5,071,527, respectively and the disclosures of which are herein incorporated by reference. Other electrical properties measured may also include capacitance, dielectric constant, and the like.

Figure 2:
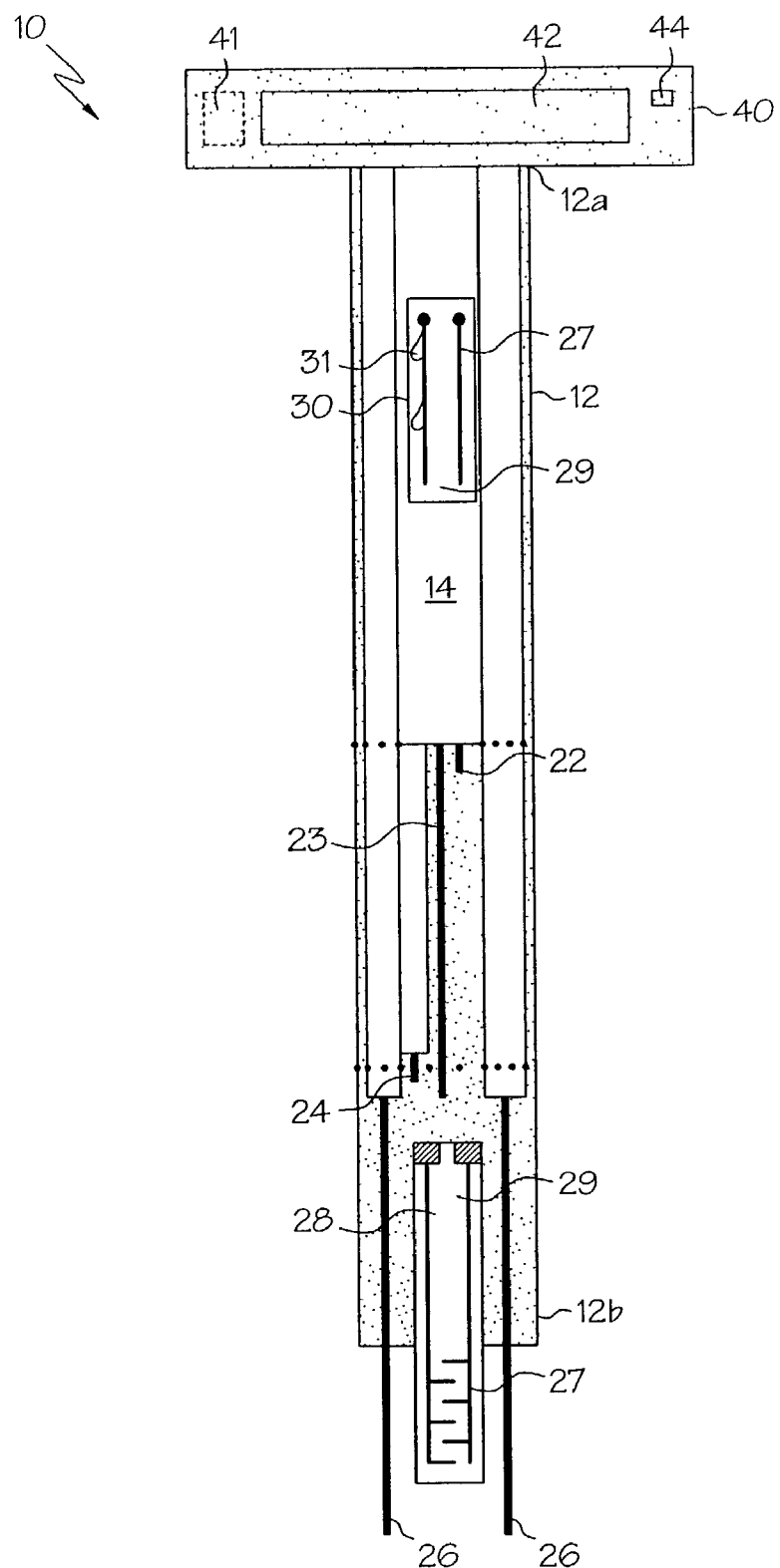
FIG. 2 is a schematic illustration of a sensor device having a plurality of vapor sensors and a plurality of liquid sensors according to another embodiment of the present invention.

As shown in FIG. 2, the liquid sensors 20 can be conductive line surfaces 27 on a nonconductive substrate 29, forming a sensor array 28 and/or can be a series of wires or wire rods 22, 23, 24, and 26. In one embodiment, insulation 14 is placed in between the liquid sensors 20 and over portions of the wire rods that are exposed to the fluid. In one embodiment, the wires or wire rods 22, 23, 24, and 26 are placed between about 0.1 mm to about 100 mm apart from one another, and more specifically about 1 mm apart from one another. In one embodiment, the sensor array 28 comprises sensors that are spaced between about 0.001 mm to about 1 mm apart, and more specifically about 0.075 mm apart. The liquid sensors 20 can be comprised of any suitable corrosive resistant, conductive material. Suitable materials include, but are not limited to, glassy carbon, platinum, gold, copper, copper alloys, nickel alloys, stainless steels, and combinations thereof. In one embodiment, the liquid sensors are made of nickel or 316 stainless steel. The insulation 14 and nonconductive substrate 29 can comprise tetrafluoroethylene, high density polyethylene, polyimide polymer used for circuit boards, alumina, any other nonconductive material dimensionally and chemically stable in the fluid environment of the operating equipment, and combinations thereof.

Referring to FIG. 2, the plurality of vapor sensors 30 contact only the fluid vapors, and are sensitive to fluid oxidation and/or condensing water droplets. Fluid oxidation or water droplets 31 typically form after stopping the equipment, such as an engine, as compounds condense from the hot fluid onto a cooler portion of the sensor device 10, such as first member end 12a. Fluid oxidation or condensing water droplets 31 can form while the engine is operating; in this case the vapor sensors 30 and point out 20 operate simultaneously. Therefore, when the engine shuts down or at any point when the fluid becomes sufficiently hot that oxidation products and/or water evaporates then condenses onto the cooler portion of the sensor device 10, condensing droplets 31 form and adhere to the vapor sensors 30. The sensor then measures the vapor parameters.

Similar to the explanation provided above for the liquid sensors 20, the vapor sensors 30 can be conductive line surfaces 27 provided on a nonconductive substrate 29, forming an array sensor, and/or can be a series of wire rods (not shown). In one embodiment, the wire rods are placed between about 0.1 mm to about 50 mm apart from one another, and more specifically about 1 mm apart from one another. In one embodiment, the sensor array comprises sensors that are spaced between about 0.001 mm to about 1 mm apart, and more specifically about 0.075 mm apart. The vapor sensors 30 can be comprised of any suitable corrosive resistant, conductive material. Suitable materials include, but are not limited to, glassy carbon, platinum, gold, copper, copper alloys, nickel alloys, copper alloys, stainless steel, and combinations thereof. In one embodiment, the vapor sensors 30 are made of nickel or 316 stainless steel. In one embodiment, insulation 14 is placed in between the vapor sensors 30 and over areas of the sensor not exposed to the fluid vapors. The insulation 14 and the nonconductive substrate 29 can be tetrafluoroethylene, high density polyethylene, polyimide polymer used for circuit boards, alumina, any other nonconductive material dimensionally and chemically stable in the fluid environment of the operating equipment, and combinations thereof.

Figure 3:
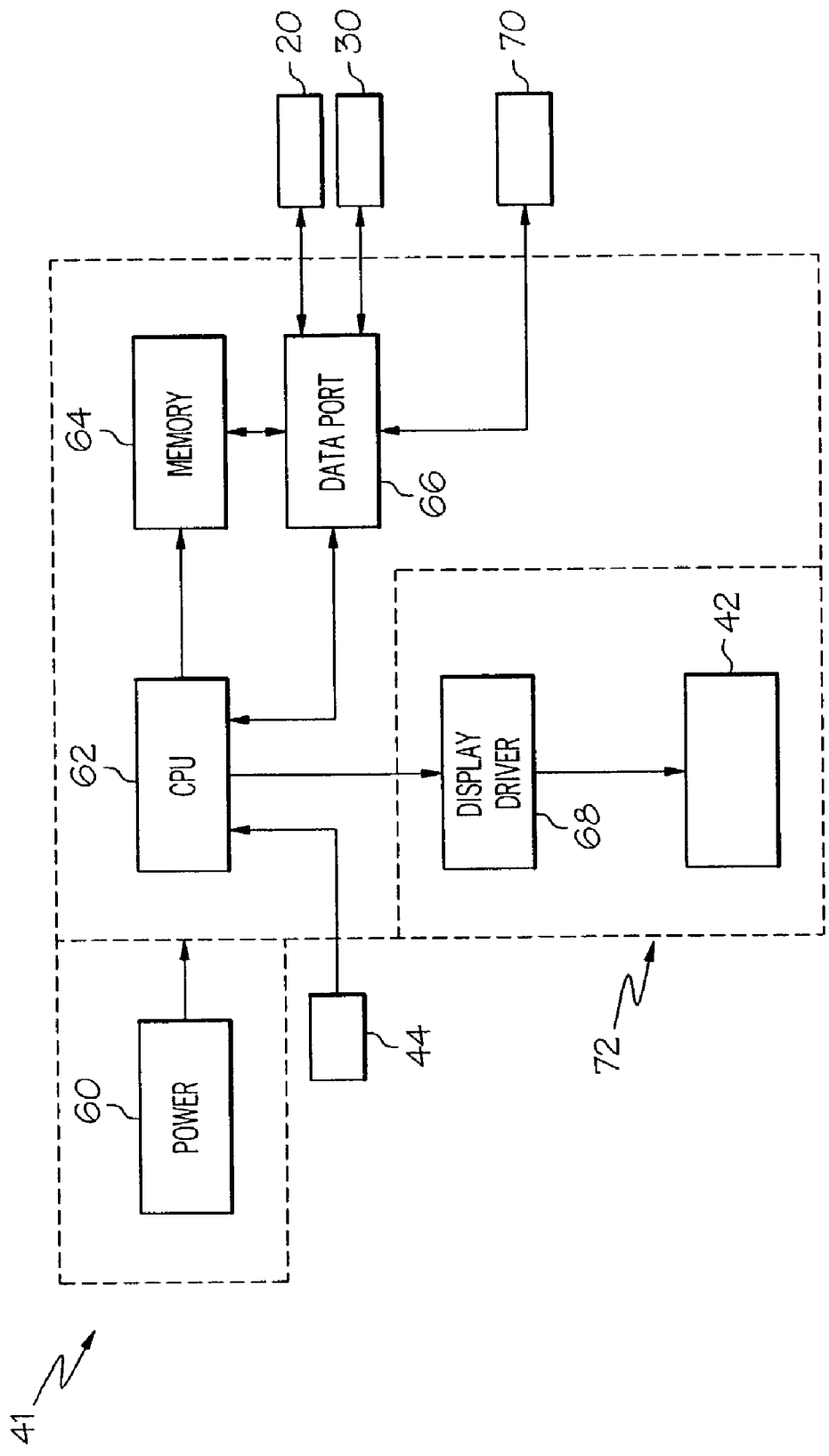
FIG. 3 is a flow chart of the sensor device's electronics according to one embodiment of the present invention.

Referring to FIGS. 2 and 3, an electronic system 40 is coupled to the first member end 12a of sensor device 10. The electronic system 40 is electrically connected to the sensors 20 and 30 and shows the overall condition and level of the fluid or can be modified to indicate a particular degradation/contamination mechanism of interest to the user. The electronic system 40 includes the electronics for the sensors 41, a readout display 42 and a reset button 44. The electronics 41 include a power source 60 which provides power to the central processing unit 62 (CPU), memory 64, data port 66, and the display system 72. The display system 72 includes the display driver 68 and the display 42. The electronics 41 calculate the condition or level of the fluid by using an algorithm based on the degradation/contamination mechanism being monitored and the measurements taken from the vapor 30 and liquid sensor 20 outputs. The CPU 62 uses the algorithm stored in memory 64, and information supplied to it from the data port 66 via sensors 20 and/or 30 to calculate the measurements for conditions that are being monitored. It is to be appreciated that data port 66 includes the necessary electronics to convert analog data from sensors 20 and/or 30 into filtered, digital information in a format suitable for handling by the CPU 62. The CPU 62 relays the calculated measurement(s) to the display driver 68. The display driver 68 then formats the measurement(s) to the display 42 such that the user may view it. The computations performed by the CPU 62 include the determination of accelerated oxidative degradation due to end of useful life or abnormal operating conditions, coolant/water contamination, soot build-up, viscosity change, accelerated wear, thermal breakdown of additives due to fires or hot spots and fluid level.

It is to be appreciated that power for the electronics 41 may be supplied by an external source, or an intended battery. Additionally, computer algorithms and other initialization data may be loaded into the memory 64 from an external computer 70 also via data port 66, if so desired. Furthermore, sensor data and computed measurements can be provided to the external computer 70 directly, from the CPU 62, sensors 20 and/or 30, and/or memory 64 via data port 66, if so desired. For example, computer 70 may be communicably coupled to the electronics 41 via a cable connection, network connection, or via a wireless technology such as radio frequency wireless.

The reset button 44 is located anywhere on the display system and may be pressed when the fluid is changed so that the device can reset the time being recorded and recognize sudden change in readings due to the fluid change. By attaching the electronic system 40 to the member 12, the sensor device 10 provides the user a quick easy look at condition of the fluid. While the electronic system 40 is shown coupled to the first member end 12a of the member 12, it is to be appreciated that the display system 40 may be coupled to the member 12 in any area convenient for the user.

Referring again to FIG. 2, when wires or wire rods 22, 23, and 24 are used as the liquid sensors 20, the level of the fluid can be approximated by the following methodology. If the fluid contacts sensor 22 and sensor 23 the fluid completes the circuit between the two adjacent wires and the FULL light on the display 42 illuminates. The display 42 is located on the display system 40. However, if the fluid level is too low to contact the sensors 22 and 23, but still contacts sensors 23 and 24 then ½ FULL illuminates in the display 42. When the fluid no longer contacts sensor 24 then the electrical circuit is broken and then ADD illuminates in the display 42. The light system illustrated in FIG. 2 could be replaced by a Liquid Crystal Display (LCD) with numerical/text readouts to conserve battery-life and to make the sensor output easier to modify. With a LCD a continuous, more accurate fluid level could be shown on display 42. When the fluid completely submerges the entire exposed portions of wire rods 26, the outputs of wire rods 26 and array 28 can be set to be equal and display 42 can be set to read 100% full. If the oil level dropped then the output of the wire rods 26 would decrease proportionally but the output of array 28 would remain constant, still completely submerged. Therefore, the ratio of the wire rods 26 output to the array 28 output could be shown by display 42 as a percentage, e.g., 70%. This reading provides an accurate level reading and rate of level decrease, allowing for timely repairs when needed. It is to be appreciated that sensors other than wire rods can be used to indicate the fluid level; however, such alternative sensors should be completely submerged to accurately indicate the fluid level as full.

In another embodiment of the present invention, a sensor array 28 having at least one magnetized line or a magnet 33 (FIG. 1) is placed behind the liquid sensors 20 when using a sensor array 28. The magnet or magnetized line 33 helps the sensor array 28 to indicate the wear rate of the monitored equipment, such as an engine, on the fluid. As the magnet or magnetized line 33 draws ferrous containing wear particles onto the sensor array 28, the sensor's output increases. When the deposited ferrous particles, and other metal particles associated with the ferrous wear debris, are in contact with both conductive lines on array 28, the circuit is completed and the sensor is electrically shorted. The difference between the output of the sensor array 28 having a magnetic field attached (off-scale) and the output of a- sensor array 28 or other liquid sensors 20 without a magnetic field (on-scale) is then attributed to the accelerated production of ferrous wear particles in the fluid by severe wear processes indicating maintenance action is necessary to repair the wearing part. The sensor array 28 can then be removed to allow inspection of the collected debris to aid the user to identify the wearing part and the severity of the wear mechanism, i.e. the composition and size of the particles. The magnet or magnetized lines 33 can be, Alnico which is a special aluminum-nickel-cobalt alloy, a ceramic such as barium or strontium ferrite, or a rare earth magnet such as Neodymium iron boron or samarium cobalt, or any other permanent magnet that retains its magnetism to temperatures above 700° F.(~371° C.).

Applied voltage waveforms, such as square, sine, and triangular waveforms, may be applied to the fluid to increase the sensitivity of the sensor device 10. The square or sine waveforms typically occur between about ±0.5V and ±15V, specifically at ±3 V. The cycle rates are typically less than 1000 Hz, specifically at 1 Hz for conductivity and 500 Hz for capacitance. Using a square or sine waveform of ±3V and 1 Hz for conductivity measurements in conjunction with the sensor device 10 increases the sensitivity of the sensor device 10 to oxidative degradation of the fluid. Using a square or sine waveform of ±3V and 500 Hz for capacitance and dielectric constant measurements in conjunction with sensor 10 increases the sensitivity of the sensor device 10 to the soot build-up and other contaminants affecting the ability of the fluid to hold an electrical charge. The triangular waveform typically occurs between ±1 and ±20 V, specifically at ±15 V and at cycle rates between 0.001 and 100 Hz, specifically 0.06 Hz. Using a triangular waveform in conjunction with the sensor device 10 causes electrolysis of the water with a resulting increase in current flow. This increase in current flow increases the sensor device's 10 sensitivity to water. The applied voltage waveforms may be supplied to the fluid by any suitable waveform generator.

Taking the sensor measurements in the liquid at different temperatures further increases the condition monitoring capabilities of the sensor device 10. For example, after the fresh oil is added to an engine, the sensor output should increase linearly or in a consistent manner with the fresh oil's temperature, indicating that the fluid is not oxidized. As the oil becomes oxidized, the liquid sensors 20 increase exponentially with temperature. Thus, the deviation from the normal linear increase from the fresh oil plot versus the temperature increase of the oxidized oil is proportional to the degree of oxidation. After a fluid change, the increase in sensor output can be established for set temperatures for the fresh oil. The established output is compared to previous fresh oil readings to ensure the proper oil was used for the change out. An algorithm can be created from the data to calculate the measurement of the output.

Figure 4:
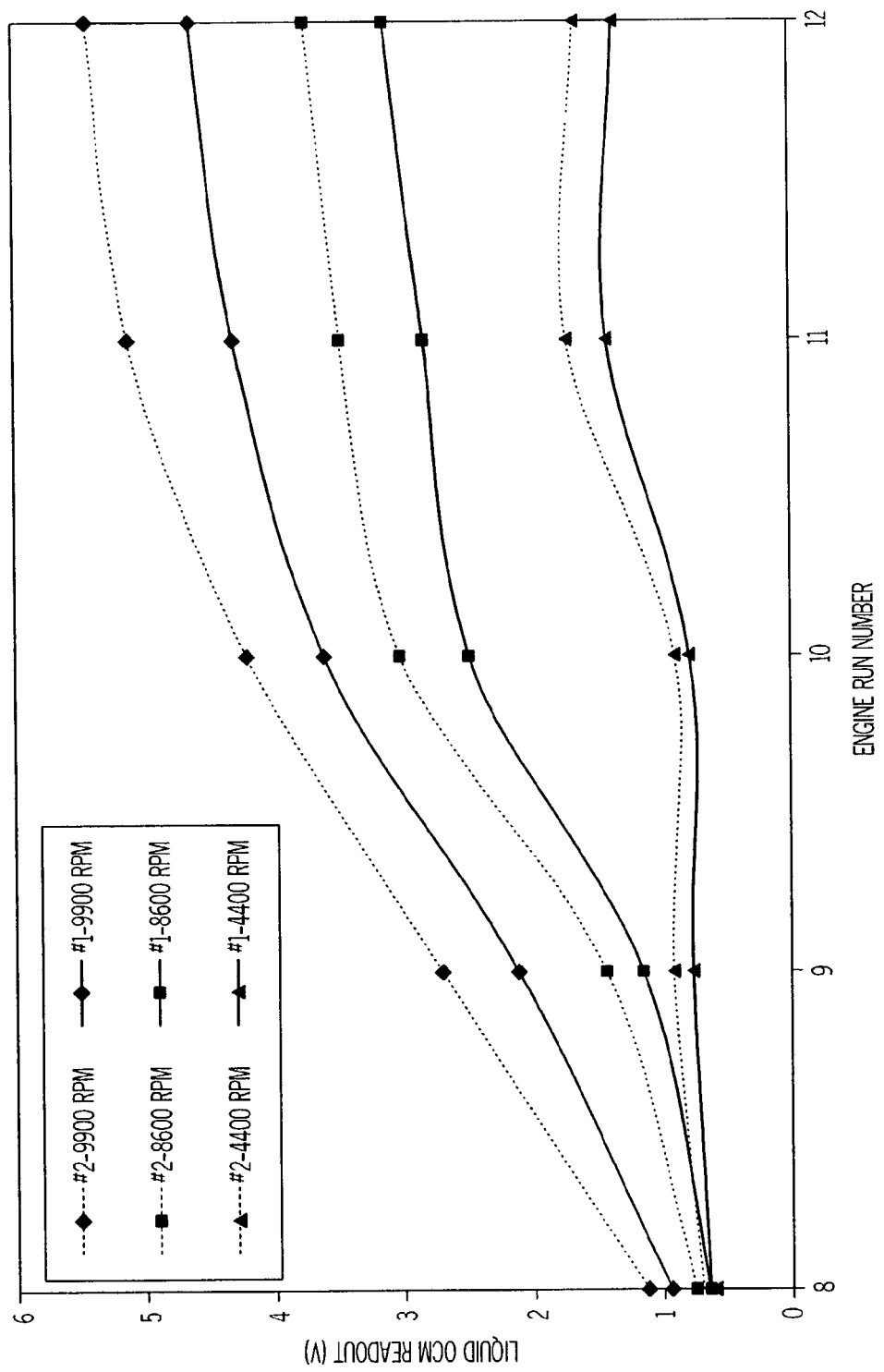
FIG. 4 is a graph showing the liquid sensor output versus temperature relationship according to the present invention.

FIG. 4 is a graph showing a sensor output versus temperature relationship for an aircraft engine accelerated oxidation test and is indicative of the degree of oxidation. In particular, the graph indicates that as the temperature increases, the output of the liquid sensor also increases. Engine Run 8 indicates the beginning of oxidation by showing outputs of liquid sensors increasing slightly with the increasing of the oil temperature as illustrated along the y-axis. The temperature of the oil increased from 260° F. (4400 RPM) up to 420° F. (9900 RPM) which resulted in an increase in the outputs of liquid sensors #1 and #2 by less than 50%. However, by Engine Run 10 as temperature increases, the outputs of the liquid sensors increased by greater than 400%. For some high temperature equipment, such as aircraft engines which undergo frequent fresh oil additions, an increase in the liquid sensor output of 50% at a preset temperature or temperature increase is considered abnormal and indicative of engine problems, i.e., cracked seal.

The rate of increase is also important. If the liquid sensor output goes from normal to off-scale in a matter of minutes, the sudden increase is indicative of a hot spot or an engine fire. For other lower temperature equipment such as diesel engines, which undergo infrequent oil additions, an increase in the liquid sensor output of 200% at a preset temperature would be tolerable and be indicative of the need for an oil change rather than an engine problem.

Taking the vapor readings as well as the liquid readings further increases the fluid condition monitoring capabilities of sensor 10. As opposed to the liquid sensor 20 readings which can be affected by detergents, antioxidants and other strongly polar additives formulated into the fluid, the vapor sensor readings are only affected by volatile oxidation compounds and where applicable, water condensation and smoke. An algorithm can be created from the data to calculate the measurement of the output.

Figure 5:
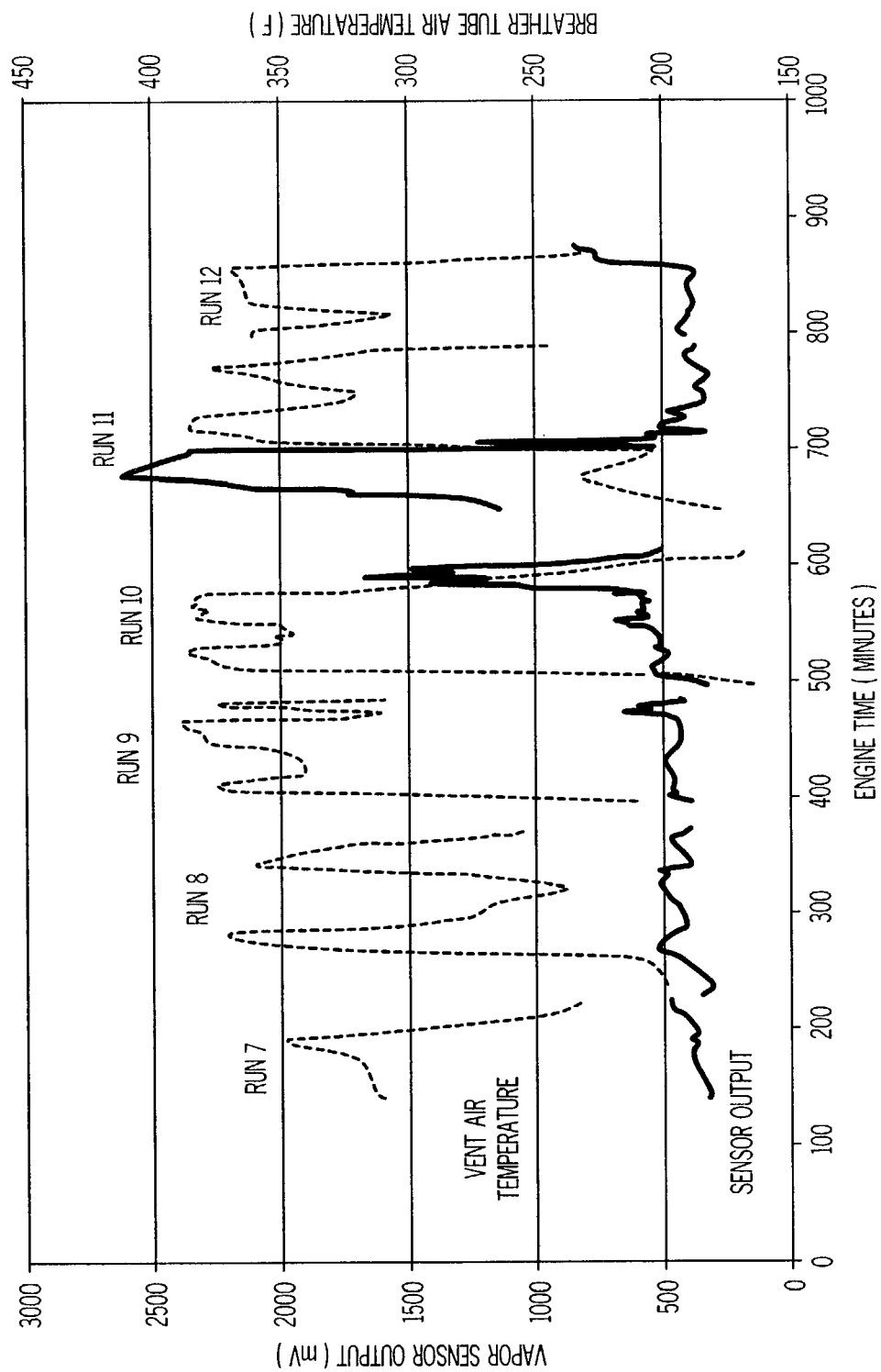
FIG. 5 is a graph showing the vapor sensor output versus temperature relationship according to the present invention.

As shown in FIG. 5 the vapor sensor readings provide an unchanged baseline until oil begins to oxidize. At the end of engine run 9 according to liquid sensors in FIG. 4, the oil is starting to oxidize as indicated by the increased output by the sensor. As opposed to the liquid sensor readings, which increase with oxidation and temperature regardless of degree of oil oxidation, the vapor sensor readings only increase when accelerated oil oxidation is occurring. The output increases as the sensor environment cools, and/or the volatile compounds condense. As opposed to oxidation products, if the vapor sensors of an aircraft engine or other high temperature application rapidly go off-scale while the equipment is operating, additive degradation products from a hot spot or smoke from a fire has been detected requiring immediate attention by the equipment operator to avoid severe component damage and equipment failure. Vapor sensors only have an output when accelerated oxidation or abnormal operating conditions are occurring and are independent of fluid composition or additive package.

Figure 6:
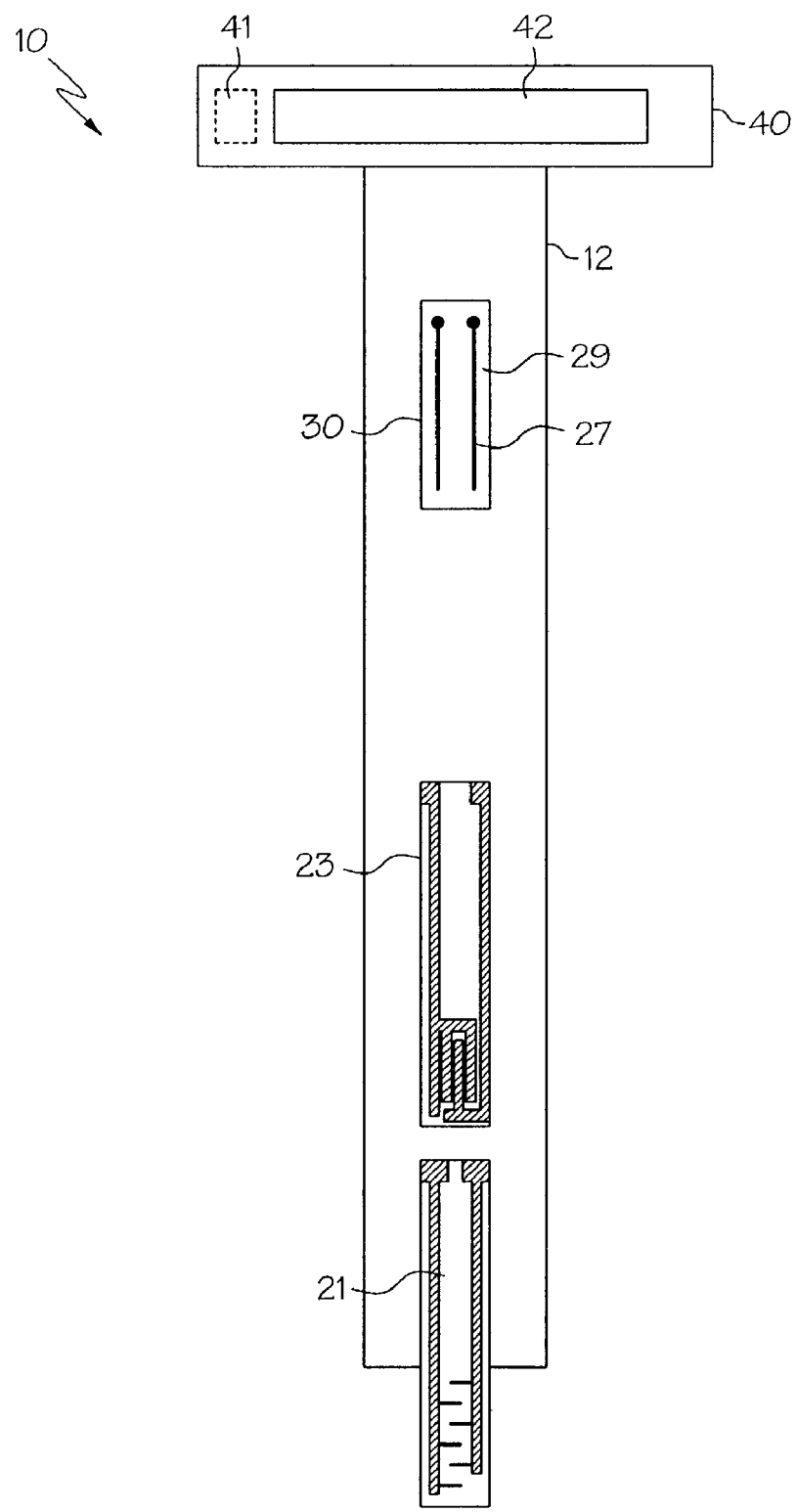
FIG. 6 is a schematic illustration of the plurality of liquid sensors in another embodiment according to the present invention.

Referring to FIG. 6, the sensor device 10 another embodiment of the present invention can measure viscosity in a stagnant system. In such an embodiment, the member 12 is placed in an area where the fluid flow, such as for example, in valves or chambers. The rate at which the fluid flows from one chamber to another, through a supply line, etc. at shut down can be used to estimate the viscosity of the in-service fluid. At shut down, as the fluid flows decrease and drain to an oil collection point, such as the oil pan, upper sensor 23 positioned in the engine becomes less covered by the fluid. This results in a decreased sensor output by sensor 23 as compared to the sensor output of sensor 21 which remains submerged in the oil. The rate at which the output of sensor 23 decreases with respect to sensor 21 is directly proportional to the viscosity of the fluid, i.e., the more viscous the oil, the slower the oil drains from the surface of senor 23 and the slower the output of sensor 23 decreases with respect to the output of sensor 21. Using a lookup table and system temperature reading, which includes a sensor precalibrated with fluids of known viscosities at known temperatures, the viscosity of the fluid is determined.

Figure 7:
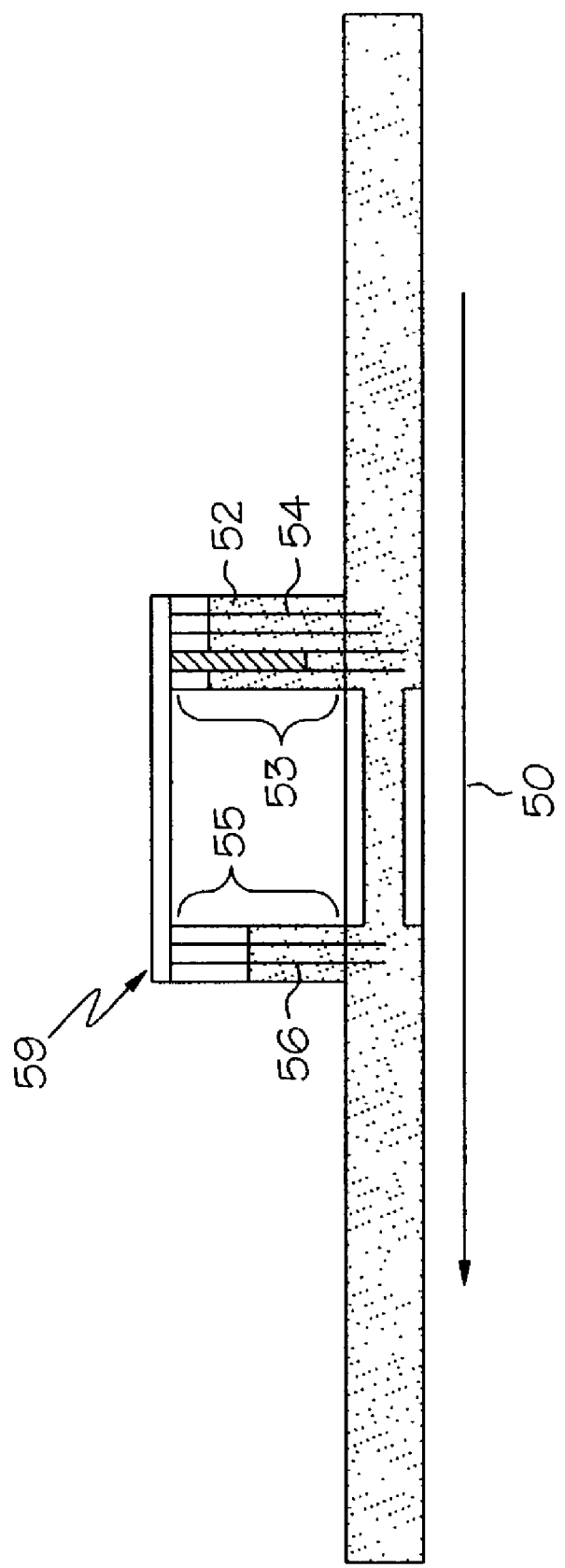
FIG. 7 is a schematic illustration of using one embodiment of the present invention to measure viscosity.

Referring to FIG. 7, a method for measuring the viscosity in a flowing system is provided. The sensor system 59 is calibrated with fluids of know viscosities at specific temperatures. A first sensor 54 is placed upstream of a flow restriction and a second sensor 56 is placed downstream. As the viscosity of fluid flowing in the direction of arrow 50 decreases, the pressure differential decreases between fluid pockets 53 and 55. The fluid level in pocket 53 decreases with respect to the fluid level in the fluid pocket 55. The output of sensor 54 in fluid pocket 53 decreases with respect to the output of sensor 56 in fluid pocket 55. The difference between the outputs of sensors 54 and 56 is directly proportional to the viscosity of the flowing fluid. This difference is compared to the calibrated measurements and calibrated with fluids of known viscosities at selected temperatures.

The liquid sensors 20 and vapor sensors 30 can also be used to detect the formation of insoluble coolant/water concentration in fluids. Liquid array sensors spaced less than 75 microns apart or vapor array sensors spaced greater than 500 microns apart or rod sensors spaced greater than 1 mm apart are typically used to detect insoluble coolant/water. For example, when coolant leaks into oil, coolant/water dissolves into oil to about 300–500 ppm concentration, depending on variables such as, dispersant additives, basestock composition, temperature, etc and is undetected by the sensors. As coolant/water accumulates, coolant/water droplets form in the oil and, depending on the operating temperature, water evaporates from the oil into vapor. When the droplets in the oil impact the liquid array sensor surface or the water vapor condenses onto the vapor array sensor surface or between the vapor rod sensors in the vapor, the droplets/water form a layer of coolant/water on the surface. When the length of the adhered film exceeds the array line spacing or bridges the rod sensor spacing then the sensor is electrically shorted and goes off scale. As soon as the coolant/water becomes insoluble in the fluid, the liquid sensor will go off-scale which indicates that water concentration is greater than 300–500 ppm. The amount of water in the fluid to cause shorting of the vapor sensors depends upon the vapor array or rod spacing, i.e., the smaller the spacing, the less condensate is needed to short the array as well as the fraction of total system water that condensates onto the vapor sensor. A baseline can be established to compare the measurement if continuous monitoring of the vapor sensor is deemed necessary.

The accumulation of soot in oils can be monitored by comparing the output of at least two of the liquid sensors. A filter or other means to separate the soot from the oil may be placed on top of the liquid array senor surface or around a liquid wire sensor so that only soot free oil can touch the sensor. At least one other sensor is not covered by the filter and is therefore exposed directly to soot containing oil. If the difference between the outputs of the filter covered sensor and the uncovered sensor remain unchanged with operating time, then the sensors are not detecting soot accumulation.

If the uncovered sensor output increases with respect to the output of the covered sensor, then the increased difference between the senor outputs is indicative of, and proportional to, soot accumulation in the fluid. The mathematical relationships between the sensor output differences and the soot level in the oil are established through precalibration of the sensors or experience with the selected equipment.

Having described the invention in detail and by reference to preferred embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A sensor device for monitoring the condition of a fluid comprising:
   a member;
   a plurality of liquid sensors provided at various lengths along said member and each comprising at least two wires or wire rods for measuring liquid parameters of the fluid, said at least two wires or wire rods are adapted to be electrically connected to one another by the fluid when said at least two wires or wire rods are immersed in and in contact with the fluid to complete an electrical circuit such that in use current passes between said at least two wires or wire rods through the fluid in order to monitor the condition of the fluid; and
   a plurality of vapor sensors in contact with vapors of the fluid for measuring vapor parameters of the fluid coupled to said member, at least one of said plurality of vapor sensors comprising conductive surfaces adapted to be electrically connected to one another by vapor of the fluid such that in use current passes between said conductive surfaces through the vapor, wherein said plurality of liquid sensors and plurality of vapor sensors are positioned a distance from one another so that said plurality of vapor sensors do not contact a liquid of the fluid.

2. A sensor device as claimed in claim 1, wherein said member is a dipstick.

3. A sensor device as claimed in claim 1, wherein said plurality of liquid sensors and said plurality of vapor sensors are adapted to operate simultaneously.

4. A sensor device as claimed in claim 1, wherein said plurality of liquid sensors further comprises at least one sensor array.

5. A sensor device as claimed in claim 4, wherein said at least one sensor array comprises sensors that are spaced between about 0.001 mm to about 1 mm apart.

6. A sensor device as claimed in claim 1, wherein said at least two wires or wire rods are spaced between about 0.1 mm and about 100 mm apart.

7. A sensor device as claimed in claim 1, wherein said plurality of vapor sensors comprises at least two conductive line surfaces provided on a nonconductive substrate.

8. A sensor device as claimed in claim 7, wherein said at least two conductive lines are spaced between about 0.1 mm and about 50 mm apart.

9. A sensor device as claimed in claim 1, wherein said plurality of vapor sensors comprises sensor arrays that are spaced between about 0.001 mm to about 1 mm apart.

10. A sensor device as claimed in claim 1, wherein said plurality of liquid sensors are formed from a conductive material selected from the group consisting of glassy carbon, platinum, gold, copper, copper alloys, nickel alloys, stainless steel, and combinations thereof.

11. A sensor device as claimed in claim 1, wherein said plurality of vapor sensors are formed from a conductive material selected from the group consisting of glassy carbon, platinum, gold) copper, copper alloys, nickel alloys, stainless steel, and combinations thereof.

12. A sensor device as claimed in claim 1, wherein said sensor device is adapted to measure fluid level, viscosity, temperature, electrical conductivity, electrochemical activity, water contamination, wear metals, soot buildup, coolant contamination, capacitance, dielectric constant, and combinations thereof.

13. A sensor device as claimed in claim 1, wherein said member is coupled to a fluid is selected from the group consisting of lubricating oils, transmission fluids, hydraulic fluids, transformer oils, metal working fluids, cooking oils, and combinations thereof.

14. A sensor device as claimed in claim 1, wherein said sensor device further comprises a magnet positioned behind one of said plurality of liquid sensors, said sensor device is adapted to measure a difference between outputs of said one of the liquid sensors having said magnet and remaining ones of said plurality of liquid sensors without said magnet, said difference being indicative of equipment wear detected by the sensor device.

15. A sensor device as claimed in claim 14, wherein said magnet is a magnetized line of a material which retains its magnetism to temperatures above about 700° F.(371° C.).

16. A sensor device as claimed in claim 1, wherein said sensor device further comprises an electronic system coupled to said member, said electronic system comprises electronics for said plurality of liquid sensors and said plurality of vapor sensors, and a readout display.

17. A sensor device as claimed in claim 1, wherein said plurality of vapor sensors comprises at least two wires or wire rods.

18. A sensor device as claimed in claim 17, wherein said at least two wires or wire rods are spaced between about 0.1 mm and about 50 mm apart.

19. A sensor device for monitoring the condition of a fluid comprising:
   a member;
   a plurality of liquid sensors for measuring liquid parameters of the fluid coupled to said member, said plurality of liquid sensors comprise at least one sensor array having conductive surfaces, said conductive surfaces adapted to be electrically connected to one another by the fluid when said conductive surfaces are immersed in and in contact with the fluid to complete an electrical circuit such that in use current passes between said conductive surfaces of said at least one sensor array through the fluid in order to monitor the condition of the fluid; and
   a plurality of vapor sensors in contact with vapors of the fluid for measuring vapor parameters of the fluid coupled to said member, each of said plurality of vapor sensors comprising at least two wires or wire rods adapted to be electrically connected to one another by vapor of the fluid such that in use current passes between said at least two wires or wire rods through the vapor, wherein said plurality of liquid sensors and plurality of vapor sensors are positioned a distance from one another so that said plurality of vapor sensors do not contact a liquid of the fluid.

20. A sensor device as claimed in claim 19, further comprising an electronic system coupled to said member, said electronic system comprises electronics for said plurality of liquid sensors and said plurality of vapor sensors, and a readout display.

21. A sensor device as claimed in claim 19, wherein said conductive surfaces of said at least one sensor array are spaced between about 0.001 mm to about 1 mm apart.

22. A sensor device as claimed in claim 19, wherein said plurality of liquid sensors further comprises at least one wire or wire rod.

23. A sensor device as claimed in claim 19, wherein said plurality of vapor sensors comprises at least two wires or wire rods.

24. A sensor device as claimed in claim 19, wherein said plurality of vapor sensors further comprises at least one sensor array.

25. A sensor device as claimed in claim 24, wherein said at least one sensor array comprises conductive surfaces that are spaced between about 0.001 mm to about 1 mm apart.

26. A sensor device for monitoring the condition of a fluid comprising:
   a member;
   a plurality of liquid sensors having conductive surfaces for measuring liquid parameters of the fluid coupled to said member, said conductive surfaces adapted to be electrically connected to one another by the fluid when said conductive surfaces are immersed in and in contact wit the fluid to complete an electrical circuit such that in use current passes between said conductive surfaces through the fluid in order to monitor the condition of the fluid; and
   a plurality of vapor sensors comprising at least one sensor array in direct contact with vapors of the fluid for measuring vapor parameters of the fluid coupled to said member, at least one of said plurality of vapor sensors comprising conductive surfaces adapted to be electrically connected to one another by vapor of the fluid such that in use current passes between said conductive surfaces through the vapor, wherein said plurality of liquid sensors and plurality of vapor sensors are positioned a distance from one another so that said plurality of vapor sensors do not contact a liquid of the fluid.

27. A sensor device as claimed in claim 26, wherein said at least one sensor array comprises sensors that are spaced between about 0.001 mm to about 1 mm apart.

28. A sensor device for monitoring the condition of a fluid comprising:
   a member;
   a plurality of liquid sensors having conductive surfaces for measuring liquid parameters of the fluid coupled to said member, said conductive surfaces of each liquid sensor adapted to be electrically connected to one another by the fluid when said conductive surfaces are immersed in and in contact with the fluid to complete an electrical circuit such that current may pass between said conductive surfaces through the fluid in order to monitor the condition of the fluid;
   a plurality of vapor sensors in direct contact with vapors of the fluid for measuring vapor parameters of the fluid coupled to said member, each of said plurality of vapor sensors comprising at least two conductive surfaces adapted to be electrically connected to one another by vapor of the fluid such that in use current passes between said at least two conductive surfaces trough the vapor, wherein said plurality of liquid sensors and plurality of vapor sensors are positioned a distance from one another so that said plurality of vapor sensors do not contact a liquid of the fluid; and
   a display system.

29. A method for monitoring the condition of a fluid comprising:
   providing a sensor device having a plurality of liquid sensors and a plurality of vapor sensors on a member, each of said plurality of liquid sensors have conductive surfaces adapted to be electrically connected to one another by the fluid when said conductive surfaces are immersed in and in contact with the fluid to complete an electrical circuit such that current may pass between said conductive surfaces of each liquid sensor through the fluid in order to monitor the condition of the fluid, said plurality of vapor sensors are in direct contact with vapors of the fluid for measuring vapor parameters of the fluid, each of said plurality of vapor sensors comprising at least two conductive surfaces adapted to be electrically connected to one another by vapor of the fluid such that in use current passes between said conductive surfaces through the vapor
   placing a portion of said member in the fluid such that said plurality of liquid sensors are immersed in and in contact with said fluid to make the electrical connection therebetween, and wherein said plurality of vapor sensors are in direct contact with the vapors of the fluid but do not come in contact with a liquid of the fluid;
   measuring at least one parameter of said fluid by detecting current passing between said conductive surfaces of each liquid sensor through the fluid; and
   determining a condition of said fluid selected from the group consisting of fluid level, viscosity, temperature, electrical conductivity, electrochemical activity, water contamination, wear metals, soot buildup, coolant contamination, capacitance, dielectric constant, and combinations thereof by analyzing measurements of said fluid using an algorithm based on said measurements of said plurality of liquid sensors and said plurality of vapor sensors.

30. A method as claimed in claim 29, wherein said method further comprises applying a square waveform to said fluid.

31. A method as claimed in claim 29, wherein said method further comprises applying a triangular waveform to said fluid.

32. A method as claimed in claim 29, wherein said method further comprises applying a sine waveform to said fluid.

33. A method as claimed in claim 29, wherein said method further comprises varying the temperature of the fluid.

34. A method as claimed in claim 29, further comprises displaying said condition of said fluid.

* * * * *

UNITED STATES PATENT AND TRADEMARK OFFICE
CERTIFICATE OF CORRECTION

PATENT NO. : 7,043,967 B2
APPLICATION NO. : 10/260754
DATED : May 16, 2006
INVENTOR(S) : Kauffman et al.

It is certified that error appears in the above-identified patent and that said Letters Patent is hereby corrected as shown below:

Col. 4, line 24, "point out" should read --liquid sensors--;

Col. 5, line 19, "intended" should read --included--;

Col. 6, line 9, ", on the fluid" should be deleted;

Col. 7, line 41, "until oil" should read --until the oil--;

Col. 10, line 7, "gold)" should read --gold,--; and

Col. 12, line 31, "therebetween," should read --there between,--.

Signed and Sealed this

Seventeenth Day of October, 2006

JON W. DUDAS
*Director of the United States Patent and Trademark Office*